United States Patent [19]
Uhen

[11] Patent Number: 6,103,084
[45] Date of Patent: *Aug. 15, 2000

[54] APPARATUS FOR ELECTROPORATION

[75] Inventor: David Alan Uhen, Burlington, Wis.

[73] Assignee: Eppendorf Netheler-Hinz GmbH, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/469,967

[22] Filed: Jun. 6, 1995

[51] Int. Cl.$^7$ .............................. B01D 61/42; B01D 57/02
[52] U.S. Cl. ......................... 204/606; 204/456; 204/607; 204/608; 204/609; 204/612; 435/291; 435/173; 435/287; 435/289; 935/52; 935/89; 935/93
[58] Field of Search .................................... 435/291, 173, 435/289, 287; 935/52, 89, 93; 204/299 R, 180.1, 183.1

[56] References Cited

U.S. PATENT DOCUMENTS

| | | |
|---|---|---|
| 3,898,410 | 8/1975 | Peters, Jr. . |
| 4,081,340 | 3/1978 | Zimmermann et al. . |
| 4,571,535 | 2/1986 | Gyugyi . |
| 4,750,100 | 6/1988 | Ragsdale . |
| 4,848,355 | 7/1989 | Nakamura et al. . |
| 4,910,140 | 3/1990 | Dower . |
| 4,946,793 | 8/1990 | Marshall, III ............................ 435/291 |
| 5,186,800 | 2/1993 | Dower . |
| 5,676,646 | 10/1997 | Hofmann et al. . |

FOREIGN PATENT DOCUMENTS

| | | |
|---|---|---|
| 967569 | 8/1964 | United Kingdom . |
| 1198111 | 7/1970 | United Kingdom . |
| WO 87/02383 | 4/1987 | WIPO . |

OTHER PUBLICATIONS

Machl, T., and Robinson, J.K., "Comparison of Electrical Versus Chemical Transformation Techniques," Biomedical Products, (May 1995).
"SCR Manual," General Electric, Fifth Edition, pp. 149–153, 158–159, 162–165, and 444–447;.
"Electrostatic Discharge Simulator Model ESS–630A," Noise Laboratory Ltd.;.
Alberts, Bruce, et al., "Molecular Biology of the Cell," Garland Publishing Inc., New York, p. 923 (1983);.
Davis, Bernard D. et al, "Microbiology," Harper & Row, pp. 34 and 878 (1968);.
MacNeil, Douglas J., "Introduction of Plasmid DNA into *Streptomyces lividans* by Electroporation," FEMS Microbiol. Lett. 42:239–244 (1987);.

Miller, Jeff F. et al., "High–Voltage Electroporation of Bacteria: Genetic Transformation of *Campylobacter jejuni* with Plasmid DNA," Proc. Natl. Acad. Sci. USA 85:856–860 (1988);.
Shivarova, N., et al., "Microbiological Implications of Electric Field Effects," Zeitschrift Allge. Mikro. 23(9):595–599 (1983);.
Potter, Huntington, et al., "Enhancer–Dependent Expression of Human κ Immunoglobulin Genes Introduced into Mouse Pre–B Lymphocytes by Electroporation," Proc. Natl. Acad. Sci. USA 81:7161–7165 (1984);.
Dower, Bill, "Electro–Transformation of Intact Bacterial Cells," Molecular Biology Reports 1(1): p5 (1987);.
Harlander, Susan K., "Transformation of *Streptococcus lactis* by Electroporation," Streptococal Genetics, pp. 229–233 (1987);.
Chassy, Bruce M., et al., "Transformation of *Lactobacillus casei* by Electroporation," FEMS Microbiol. Lett. 44: 173–177 (1987);.
Powell, Ian B., et al., "A Simple and Rapid Method for Genetic Transformation of Lactic Streptococci by Electroporation," Appl. Environ. Microbiol. 54(3):655–660 (1988);.
BioRad, "Gene Pulser™ Transfection Apparatus Operating Instructions and Applications Guide" pp. 1–28 (Jan. 1987).

*Primary Examiner*—James O. Wilson
*Attorney, Agent, or Firm*—Medlen & Carroll, LLP

[57] ABSTRACT

An apparatus for electroporation stores a level of charge, specified by a user, on a capacitor, which is delivered to a cuvette through an optically isolated high voltage switch. The capacitor is charged through a charging system, including a current mode pulse width modulation control circuit, which monitors the current in the primary winding of a transformer and supplies a pulse width modulated signal, limiting the current on every pulse to a level set by the microcontroller, to the controlling transistor in order to generate the drive to the primary winding of the transformer. A controlled amount of energy is transferred through each pulse to the capacitor. The microcontroller monitors the voltage on the capacitor up to a threshold level to predict the number of pulses necessary to store the requested amount of charge on the capacitor. The microcontroller will then count the number of pulses until the number of pulses necessary to store the requested amount of charge on the capacitor has been reached. At this point the requested voltage is delivered to the cuvette through the optically isolated high voltage switch comprised of sensitive gate SCRs coupled together in series. The voltage and current at the cuvette are monitored and input to the microcontroller so that the impedance at the cuvette is calculated by the microcontroller and errors in the composition of the solution within the cuvette are detected.

8 Claims, 15 Drawing Sheets

APPARATUS FOR ELECTROPORATION

FIELD OF THE INVENTION

The present invention relates to the field of electroporation or transfection and cell fusion. More particularly, the present invention relates to an apparatus and method for directing high-voltage currents to a suspension of cells and DNA.

BACKGROUND OF THE INVENTION

An electroporator uses a high-voltage electrical discharge to introduce cloned DNA into mammalian and any other cells. This method, commonly referred to as transfection, involves creating a suspension of cells in a phosphate-buffered saline (PBS) solution and adding cloned DNA. The suspension is then subjected to a high-voltage pulse from an electrical pulse generator which causes the cells to take up and express the exogenous DNA.

The amount of voltage and current required in transfection procedures depends upon the cell and DNA types, and the electrical characteristics which must be closely controlled. It has been discovered that some transfection procedures require currents of as much as 125 amps and more.

A transfection high-voltage controller is taught by Charles W. Ragsdale in U.S. Pat. No. 4,750,100. FIG. 1 of the Ragsdale patent illustrates a schematic diagram of the circuit used by Ragsdale to deliver a high-voltage pulse to a load such as a cuvette. An AC power supply is coupled to a transformer 52 through an AC switch 28 controlled by a control processor 20. A capacitor 60 is used to store the charge delivered from the transformer 52. This capacitor 60 is allowed to charge to a voltage level above the voltage level requested by a user. After the capacitor 60 has reached a voltage level sufficiently above the requested voltage, the control processor 20 will open the AC switch and the capacitor 60 gradually discharges through the resistor 61. When the charge on the capacitor 60 reaches the requested voltage level the Hi-Joule switch 16 is triggered to pass the charge on the capacitor 60 to the load 74. The Hi-Joule switch 16 is comprised of one or more semiconductor controlled rectifiers (SCR).

The transfection high-voltage controller taught by Ragsdale requires that the capacitor 60, which is used to store and deliver the charge, be overcharged. Once the capacitor 60 is overcharged sufficiently, this charge is bled off through the resistor 61, until the charge on the capacitor 60 reaches the specified level, at which time the switch 16 is triggered and the charge on the capacitor 60 is delivered to the load 74. By overcharging the capacitor 60 and then bleeding off the excess charge, the transfection high-voltage controller taught by Ragsdale is both inefficient and slow.

SUMMARY OF THE PRESENT INVENTION

An apparatus for electroporation stores a level of charge, specified by a user, on a capacitor, which is delivered to a cuvette through an optically isolated high voltage switch. The capacitor is charged through a charging system, including a current mode pulse width modulation control circuit, which monitors the current in the primary winding of a transformer and supplies a pulse width modulated signal, limiting the current on every pulse to a level set by the microcontroller, to the controlling transistor in order to generate the drive to the primary winding of the transformer. A controlled amount of energy is transferred through each pulse to the capacitor. By a "controlled amount" it is meant that a fixed or constant amount of energy is transferred through each pulse, as controlled by the microcontroller. The microcontroller monitors the voltage on the capacitor up to a threshold level to predict the number of pulses necessary to store the requested amount of charge on the capacitor. By "threshold level" it is meant either a predetermined number of pulses or a predetermined level of charge. The microcontroller will then count the number of pulses until the number of pulses necessary to store the requested amount of charge (i.e., the predetermined charge) on the capacitor has been reached. At this point the requested voltage is delivered to the cuvette through the optically isolated high voltage switch comprised of sensitive gate SCRs coupled together in series. The voltage and current at the cuvette are monitored and input to the microcontroller so that the impedance at the cuvette is calculated by the microcontroller and errors in the composition of the solution within the cuvette are detected.

DETAILED DESCRIPTION OF THE PREFERRED EMBODIMENT

Figure 1:
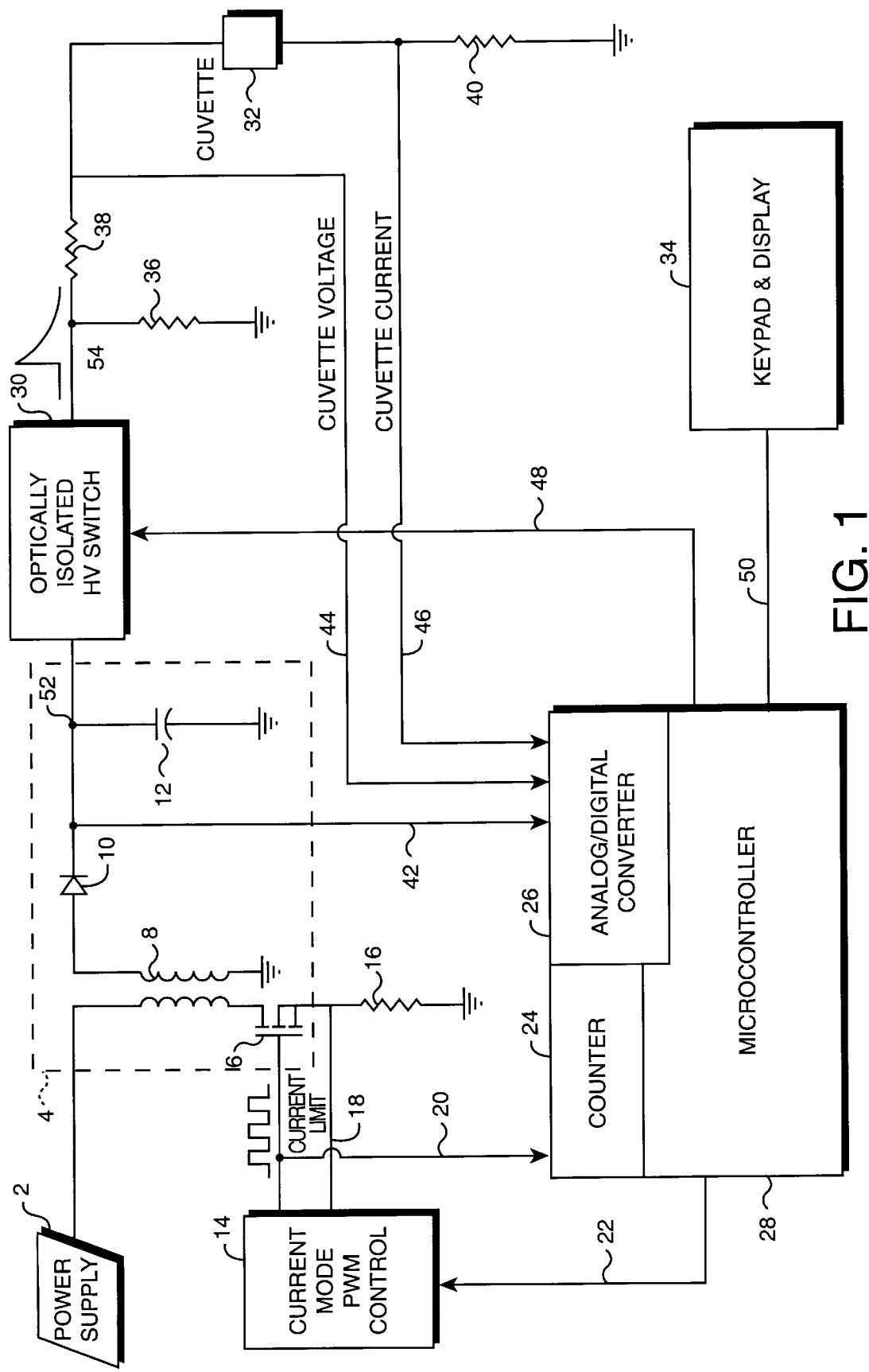
FIG. 1 illustrates a schematic block diagram of the apparatus of the present invention.

The apparatus for electroporation according to the present invention is illustrated in FIG. 1. A classic flyback power supply circuit 4 is utilized to deliver a high voltage charge to the cuvette 32 through the optically isolated high voltage switch 30. In contrast to the systems of the prior art, the apparatus of the present invention monitors the charge being delivered to and stored on the capacitor 12 only up to a threshold value. The charge per pulse, delivered to the capacitor 12 is calculated by the microcontroller 28 and the number of pulses required to store the requested amount of charge on the capacitor 12 is also calculated. The microcontroller will attempt to keep the charge stored per each pulse constant or substantially identical. Once the microcontroller 28 has calculated the number of pulses required to store the requested amount of charge on the capacitor 12, the charge stored on the capacitor 12 is not measured anymore. As soon as the number of pulses required to store the requested amount of charge on the capacitor have been sent, the microcontroller 28 activates the high voltage switch 30 and the stored charge is delivered to the cuvette 32. Thus, the inefficiencies and delays of the prior art systems are avoided.

The charging system of the present invention uses a power supply 2 which charges the capacitor 12 through the flyback power supply circuit 4 formed by the transistor 6, the transformer 8 and the diode 10. The current mode pulse width modulation control circuit 14 monitors the current in the primary winding of the transformer 8 and supplies a pulse width modulated signal, limiting the current on every pulse to a predetermined level set by the microcontroller 28, to the transistor 6 in order to generate the drive signal to the primary winding of the transformer 8. The current builds in the primary winding of the transformer 8 until the voltage across the current limit resistor 16 reaches a threshold set by the pulse width modulation control circuit 14. The transistor 6 then transfers a controlled amount of energy through each pulse to the capacitor 12. The microcontroller 28 monitors the voltage on the capacitor 12, through the Analog-to-Digital converter 26, up to a threshold level to predict the number of pulses necessary to store the requested amount of charge on the capacitor 12. The microcontroller 28 then utilizes the counter 24 to count the required number of pulses. As soon as the counter 24 has counted the required number of pulses, the optically isolated high voltage switch 30 is activated and the requested voltage is delivered to the cuvette 32.

The apparatus of the present invention also monitors the voltage and current levels at the cuvette 32. The voltage and current levels are used to calculate the impedance value at the cuvette 32 in order to detect errors in the composition of the solution and maintain the safety of the individuals operating the apparatus for electroporation. If the calculated impedance value is out of a specified range, signalling that an error condition has occurred, a user is notified through the display 34.

A power supply 2 is coupled to a first terminal of the primary winding of the transformer 8. In the preferred embodiment of the present invention, the power supply 2 is a high efficiency 24 volt DC to DC converter. As will be apparent to those skilled in the art, other types of suitable power supplies may also be utilized as the power supply 2. The preferred embodiment of the present invention is designed to generate a charge of 200 to 2500 volts DC on the capacitor 12 for delivery to the cuvette 32.

A second terminal of the primary winding of the transformer 8 is coupled to the drain of the transistor 6. In the preferred embodiment of the present invention, the transistor 6 is an n-channel enhancement-type MOSFET. As will be apparent to those skilled in the art, in an alternative embodiment, any other type of appropriate transistor may be utilized for the transistor 6.

The current mode pulse width modulation control circuit 14 is coupled to the gate of the transistor 6 and to the counter 24 through the control signal line 20, for controlling the operation of the transistor 6 and thereby controlling the current flowing through the transformer 8. The counter 24 monitors and counts the pulses on the counter signal line 20. The source and substrate of the transistor 6 are coupled to the current mode pulse width modulation control circuit 14, through the current limit signal line 18, and to a first terminal of the resistor 16. A second terminal of the resistor 16 is coupled to ground. The microcontroller 28 is coupled to the current mode pulse width modulation control circuit 14 through the control signal line 22 for controlling the operation of the current mode pulse width modulation control circuit 14.

A first terminal of the secondary winding of the transformer 8 is coupled to the anode of the diode 10. The second terminal of the secondary winding of the transformer 8 is coupled to ground. The cathode of the diode 10 is coupled to the Analog-to-Digital converter circuit 26 through the control signal line 42 and to a first terminal of the capacitor 12 for delivering a controlled amount of charge to the capacitor 12. A second terminal of the capacitor 12 is coupled to ground. The cathode of the diode 10 and the first terminal of the capacitor 12 are also coupled to a first terminal of the optically isolated high voltage switch 30.

A second terminal of the optically isolated high voltage switch 30 is coupled to a first terminal of the resistor 36 and to a first terminal of the resistor 38. A second terminal of the resistor 36 is coupled to ground. The resistor 36 and the capacitor 12 define the time constant of the energy pulse delivered to the cuvette 32, as is well known in the art. In the preferred embodiment of the present invention, the capacitor 12 is a 10 $\mu$F capacitor and the resistor 36 is a 600 ohm resistor. However, in order to vary the time constant of the sample pulse delivered to the cuvette 32, the values of the capacitor 12 and the resistor 36 may be changed.

The microcontroller 28 is coupled to the optically isolated high voltage switch 30, through the control signal line 48, for controlling the operation of the optically isolated high voltage switch 30. A second terminal of the resistor 38 is coupled to the Analog-to-Digital converter 26, through the cuvette voltage monitoring signal line 44, for monitoring the voltage level at the cuvette 32. The second terminal of the resistor 38 is also coupled to a first terminal of the cuvette 32 for delivering the charge from the capacitor 12 to the cuvette 32. A second terminal of the cuvette 32 is coupled to the Analog-to-Digital converter 26, through the cuvette current monitoring signal line 46, for monitoring the current level flowing through the cuvette 32. The second terminal of the cuvette 32 is also coupled to a first terminal of the resistor 40. A second terminal of the resistor 40 is coupled to ground.

The counter 24 and the Analog-to-Digital converter circuit 26 are integral parts of the microcontroller 28. The microcontroller 28 is also coupled to receive input from and control the operation of the keypad and display circuit 34, through the input/output signal line 50.

The control software used within the preferred embodiment of the apparatus for electroporation waits for the user to program the desired voltage level, set_voltage, to be delivered to the cuvette 32 and then to press the charge key on the keypad 34. Once the user presses the charge key on the keypad 34, the microcontroller 28 and the operating control software begin the operation of charging the capacitor 12. While the capacitor 12 is being charged a message "CHG" is displayed to the user on the display 34 to notify them that the charge is being built up and will soon be delivered to the cuvette 32. Before the operation of charging the capacitor 12 is begun, the microcontroller 28 first measures the voltage level at the capacitor 12, using the control signal line 42 and the Analog-to-Digital converter 26. This zero_voltage_level value is then used as a reference to calculate two threshold voltage levels, threshold1 and threshold2. Once the two threshold levels have been calculated, the microcontroller 28 then takes steps to begin charging the capacitor 12 by clearing the pulse counter 24 and resetting the peak detection circuit which monitors the voltage level delivered to the cuvette 32.

To begin the operation of charging the capacitor 12, the pulse width modulation control circuit 14 is turned on. The capacitor 12 is then charged and the microcontroller 28 monitors the voltage across the capacitor 12 until the voltage across the capacitor 12 reaches the first threshold value, threshold1. The number of pulses within the pulse counter 24 at the time the first threshold value is reached is then stored as the value, pulse_count1. The capacitor 12 is then continuously charged, with the microcontroller 28 monitoring the voltage across the capacitor 12 until the voltage across the capacitor 12 equals the second threshold value, threshold2. The number of pulses within the pulse counter 24 at the time the second threshold value is reached is then stored as the value, pulse_count2. The total number of pulses, pulse_count_final, which will be necessary to store the desired voltage, set_voltage, is then calculated using the threshold values, threshold1 and threshold2, the pulse count values, pulse_count1 and pulse_count2, and the following formula:

pulse_count_final=pulse_count2+(set_voltage_threshold2)× (pulse_count2—pulse_count1)/(threshold2_threshold1)

This formula calculates the charge per pulse delivered to the capacitor 12 between the first and second threshold levels, threshold1 and threshold2. This charge per pulse value is then multiplied by the remaining charge to be stored on the capacitor 12 to reach the desired voltage level, thereby forming a remaining number of pulses value. This remaining number of pulses value is added to the number of pulses already stored with the result yielding the total number of pulses required value. Once the total number of pulses required to store the desired amount of charge on the capacitor 12 is calculated, the microcontroller 28 does not monitor the voltage level of the capacitor 12. The number of pulses is monitored until the total number of pulses necessary to store the desired amount of charge has been delivered to the capacitor 12.

Once the total number of pulses necessary to store the desired amount of charge has been delivered to the capacitor 12, the pulse width modulation control circuit 14 is turned off and the discharge pulse is triggered by activating the optically isolated high voltage switch 30. The peak voltage level delivered to the cuvette 32 is measured and communicated to the microcontroller 28 through the cuvette voltage monitoring signal line 44. The level of the current flowing through the cuvette 32 is measured and communicated to the microcontroller 28 through the cuvette current monitoring signal line 46. The discharge curve and the time constant for the amount of charge delivered to the cuvette is then calculated using the analog-to-digital converter 26. The values of the peak voltage delivered to the cuvette 32, the time constant and the voltage programmed by the user are then displayed on the display 34.

During operation of the apparatus for electroporation, a user will set up the suspension of cells within the PBS solution and add cloned DNA in the cuvette 32. This operating individual then uses the keypad 34 and programs the desired voltage level to be delivered to the cuvette 32. This desired voltage level is communicated to the microcontroller 28 through the input/output signal line 50. The microcontroller 28 then initiates the operation of the current mode pulse width modulation control circuit 14. The current mode pulse width modulation control circuit 14 supplies a pulse width modulated control signal to the transistor 6. This pulse width modulated control signal controls the operation of the transistor 6 and effectively controls the time period over which the transistor 6 is conducting. This time period is specified by the microcontroller 28. Accordingly, with each pulse from the current mode pulse width modulation control circuit 14, a controlled amount of current flows through the primary winding of the transformer 8 and through the transistor 6. This controlled amount of current is monitored by the current mode pulse width modulation control circuit 14. With each pulse of a controlled amount of current which flows through the primary winding of the transformer 8, a controlled amount of energy is transferred to the capacitor 12. This controlled amount of energy transferred to the capacitor 12 is monitored by the microcontroller 28, through the control signal line 42 and the Analog-to-Digital converter 26. With each pulse output from the current mode pulse width modulation control circuit 14, the counter 24 is incremented. After monitoring a predetermined number of pulses, the microcontroller 28 calculates the energy per pulse which is being delivered to the capacitor 12 by measuring the charge stored on the capacitor 12 and dividing that value by the number of pulses which have been sent to the capacitor 12. In the preferred embodiment, as described above, the microcontroller 28 calculates the energy per pulse which is delivered to the capacitor 12 between the first and second threshold values, threshold1 and threshold2. Alternatively, the microcontroller 28 will measure the charge stored on the capacitor 12 up until a specified percentage or threshold amount of charge is stored on the capacitor 12. Once this threshold amount of charge is measured on the capacitor 12, the energy per pulse value is calculated. Using the calculated energy per pulse the microcontroller 28 then calculates the number of pulses necessary to deliver the total programmed amount of charge to the capacitor 12. The microcontroller 28 then does not monitor the energy delivered to the capacitor 12 any longer. The microcontroller 28 does monitor the value of the counter 24 and will activate the optically isolated high voltage switch 30, when the value of the counter 24 is equal to the number of pulses necessary to deliver the programmed charge to the capacitor 12, thereby delivering the stored charge from the capacitor 12 to the cuvette 32. Thus, when the value of the counter 24 is equal to the number of pulses necessary to deliver the total programmed amount of charge to the capacitor 12, the capacitor 12 will have the total programmed amount of charge stored on it. This total amount of charge is transferred to the cuvette 32 when the optically isolated high voltage switch 30 is activated.

The voltage level at the cuvette 32 is measured and communicated to the microcontroller 28 through the cuvette voltage monitoring signal line 44 which transmits an analog value to the Analog-to-Digital converter 26. This analog voltage value is converted into a digital value by the Analog-to-Digital converter 26 and communicated to the microcontroller 28. The level of the current flowing through the cuvette 32 is measured and communicated to the microcontroller 28 through the cuvette current monitoring signal line 46 which transmits an analog value to the Analog-to-Digital converter 26. This analog current value is also converted into a digital value by the Analog-to-Digital converter 26 and communicated to the microcontroller 28. The microcontroller 28 then utilizes the measured voltage and current levels to calculate the impedance at the cuvette 32. In the preferred embodiment of the apparatus of the present invention, the microcontroller 28 transmits this impedance value to the display 34 and instructs the display 34 to display the impedance value. In alternative embodiments, the measured voltage and current levels at the cuvette 32 may also be displayed.

The microcontroller 28 also monitors the calculated impedance value in order to ensure that conditions for proper operation exist at the cuvette 32. If the calculated impedance value is not within an acceptable range, the microcontroller 28 will notify the user through the display 34. For normal operation of the preferred embodiment, all sample impedance values above 3300 ohms are within the acceptable range. As will be apparent to those skilled in the art, the acceptable range for the calculated impedance value may be changed in alternative embodiments in order to accommodate varying conditions. If the sample impedance value is not within the acceptable range, a message is then displayed on the display 34, thereby notifying the user that a sample impedance value outside of the acceptable range has been detected. Errors in the makeup of the solution within the cuvette 32 will cause the sample impedance value to be outside of the acceptable range.

Figure 2:
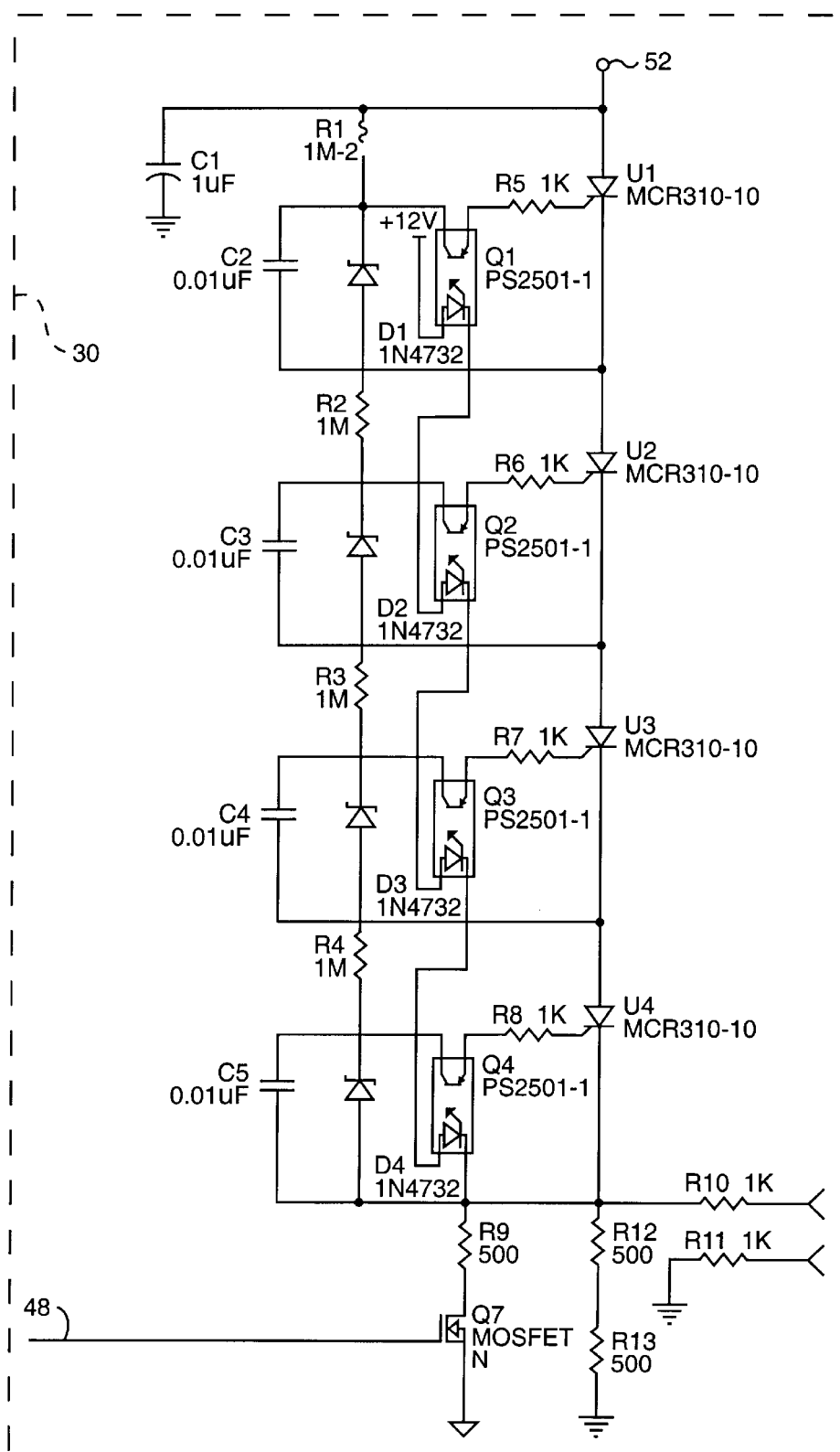
FIG. 2 illustrates a schematic circuit diagram of the preferred embodiment of the optically isolated high voltage switch of the present invention.

The optically isolated high voltage switch 30 employed by the apparatus of the present invention may comprise a single semiconductor controller rectifier (SCR) or multiple SCRs, as is well known in the art. In the preferred embodiment of the present invention, four SCRs are coupled together in series, as illustrated in FIG. 2. The optically isolated high voltage switch 30 is coupled to the capacitor 12 through the node 52 and to the cuvette 32 through the node 54. The control signal line 48 is coupled to the gate of the transistor 152 for triggering the optical trigger circuits 108, 110, 112 and 114 and thereby activating the SCRs 100, 102, 104 and 106. In the preferred embodiment of the present invention, the transistor 152 is an n-channel enhancement-type MOSFET. The anode of the SCR 100 is coupled to the node 52, to a first terminal of the resistor 134 and to a first terminal of the capacitor 116. A second terminal of the resistor 134 is coupled to the optical triggering circuit 108, to the cathode of the zener diode 126 and to a first terminal of the capacitor 118. The optical triggering circuit 108 is coupled to a first terminal of the resistor 136. A second terminal of the resistor 136 is coupled to the gate of the SCR 100. The cathode of the SCR 100 is coupled to a second terminal of the capacitor 118, to the anode of the zener diode 126, to a first terminal of the resistor 154 and to the anode of the SCR 102. The optical triggering circuit 108 is also coupled to the power supply 160 and to the optical triggering circuit 110.

A second terminal of the resistor 154 is coupled to a first terminal of the capacitor 120, to the cathode of the zener diode 128 and to the optical triggering circuit 110. The optical triggering circuit 110 is also coupled to a first terminal of the resistor 138. A second terminal of the resistor 138 is coupled to the gate of the SCR 102. The cathode of the SCR 102 is coupled to the second terminal of the capacitor 120, to the anode of the zener diode 128, to a first terminal of the resistor 156 and to the anode of the SCR 104. The optical triggering circuit 110 is also coupled to the optical triggering circuit 112.

A second terminal of the resistor 156 is coupled to a first terminal of the capacitor 122, to the cathode of the zener diode 130 and to the optical triggering circuit 112. The optical triggering circuit 112 is also coupled to a first terminal of the resistor 140. A second terminal of the resistor 140 is coupled to the gate of the SCR 104. The cathode of the SCR 104 is coupled to a second terminal of the capacitor 122, to the anode of the zener diode 130, to a first terminal of the resistor 158 and to the anode of the SCR 106. The optical triggering circuit 112 is also coupled to the optical triggering circuit 114.

A second terminal of the resistor 158 is coupled to a first terminal of the capacitor 124, to the cathode of the zener diode 132 and to the optical triggering circuit 114. The optical triggering circuit 114 is also coupled to a first terminal of the resistor 142. A second terminal of the resistor 142 is coupled to the gate of the SCR 106. The cathode of the SCR 106 is coupled to a second terminal of the capacitor 124, to the anode of the zener diode 132, to a first terminal of the resistor 146 and to a first terminal of the resistor 150. A second terminal of the resistor 146 is coupled to a first terminal of the resistor 148. A second terminal of the resistor 148 is coupled to ground. The optical triggering circuit 114 is coupled to a first terminal of the resistor 144. A second terminal of the resistor 144 is coupled to the drain of the transistor 152. The source and substrate of the transistor 152 is coupled to ground. A second terminal of the resistor 150 is coupled to the node 54.

By using the circuit, as illustrated in FIG. 2, for the optically isolated high voltage switch 30, much less current is necessary to trigger the switch 30. Coupling a resistor and a zener diode in series across each of the SCRs 100, 102, 104 and 106 provides a static equalization of voltage across the SCRS, so that each SCR 100, 102, 104 and 106 will never see more than ¼ of the total voltage being delivered to the cuvette 32. Therefore, in the preferred embodiment of the present invention, the SCRs 100, 102, 104 and 106 will each see a maximum of 625 volts. A charge is generated on each capacitor 118, 120, 122 and 124, which is shunted to the gate of each SCR 100, 102, 104 and 106, when the respective optical triggering circuits 108, 110, 112 and 114 are activated. The optical triggering circuits 108, 110, 112 and 114 are coupled together in series in order to facilitate simultaneous triggering of the SCRs 100, 102, 104 and 106.

In the preferred embodiment of the present invention, the capacitor 116 is 10 $\mu$F and the capacitors 118, 120, 122 and 124 are all 0.001 $\mu$F. In the preferred embodiment of the present invention, the resistors 134, 154, 156 and 158 are all 1 Mega-ohm resistors. In the preferred embodiment of the present invention, the resistors 136, 138, 140, 142 and 150 are all 1 Kilo-ohm resistors. In the preferred embodiment of the present invention, the resistors 144, 146 and 148 are all 300 ohm resistors.

Figure 3A:
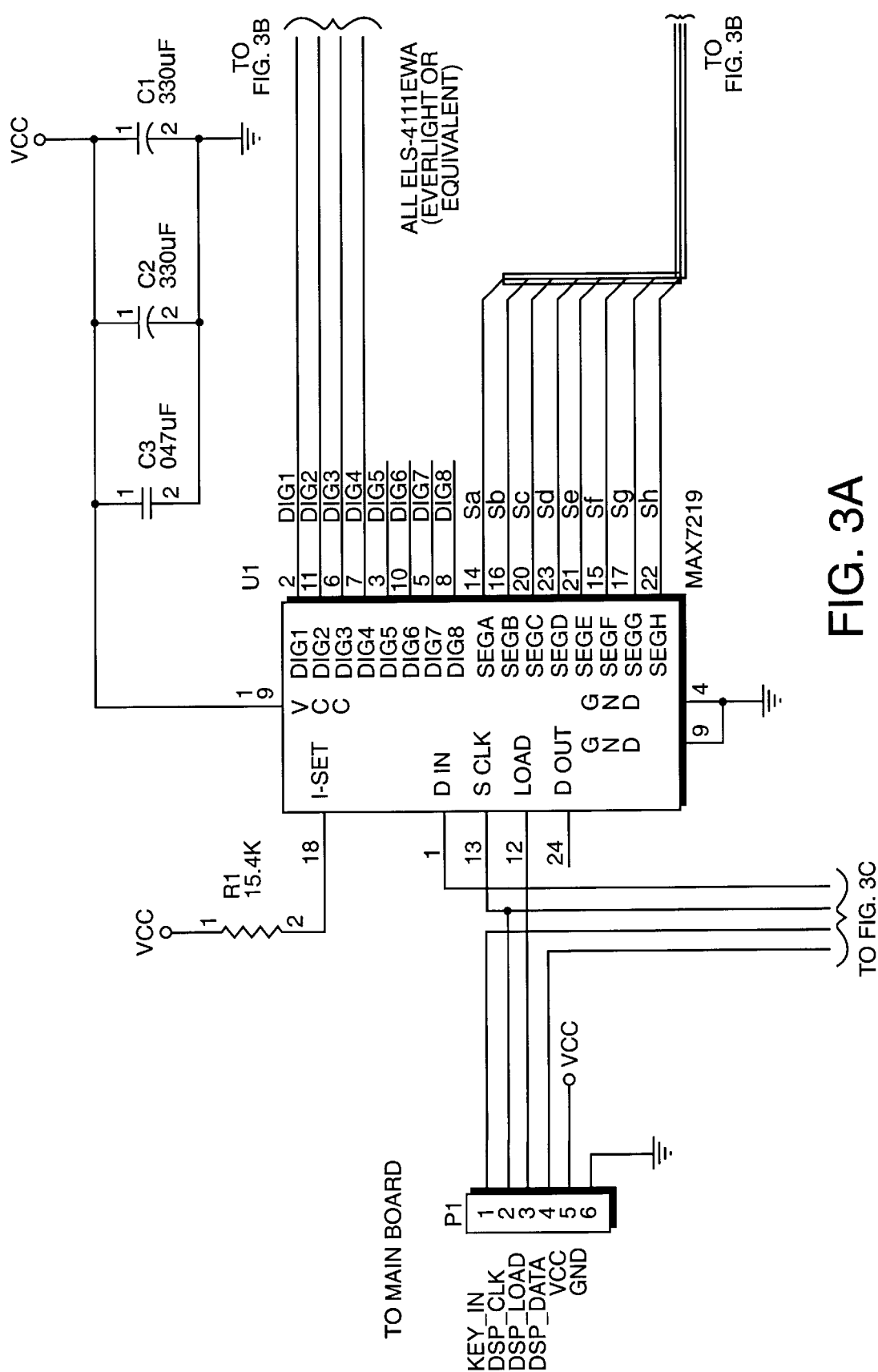
FIG. 3 illustrates a block diagram schematic of the display board circuitry of the preferred embodiment of the present invention.
Figure 3B:
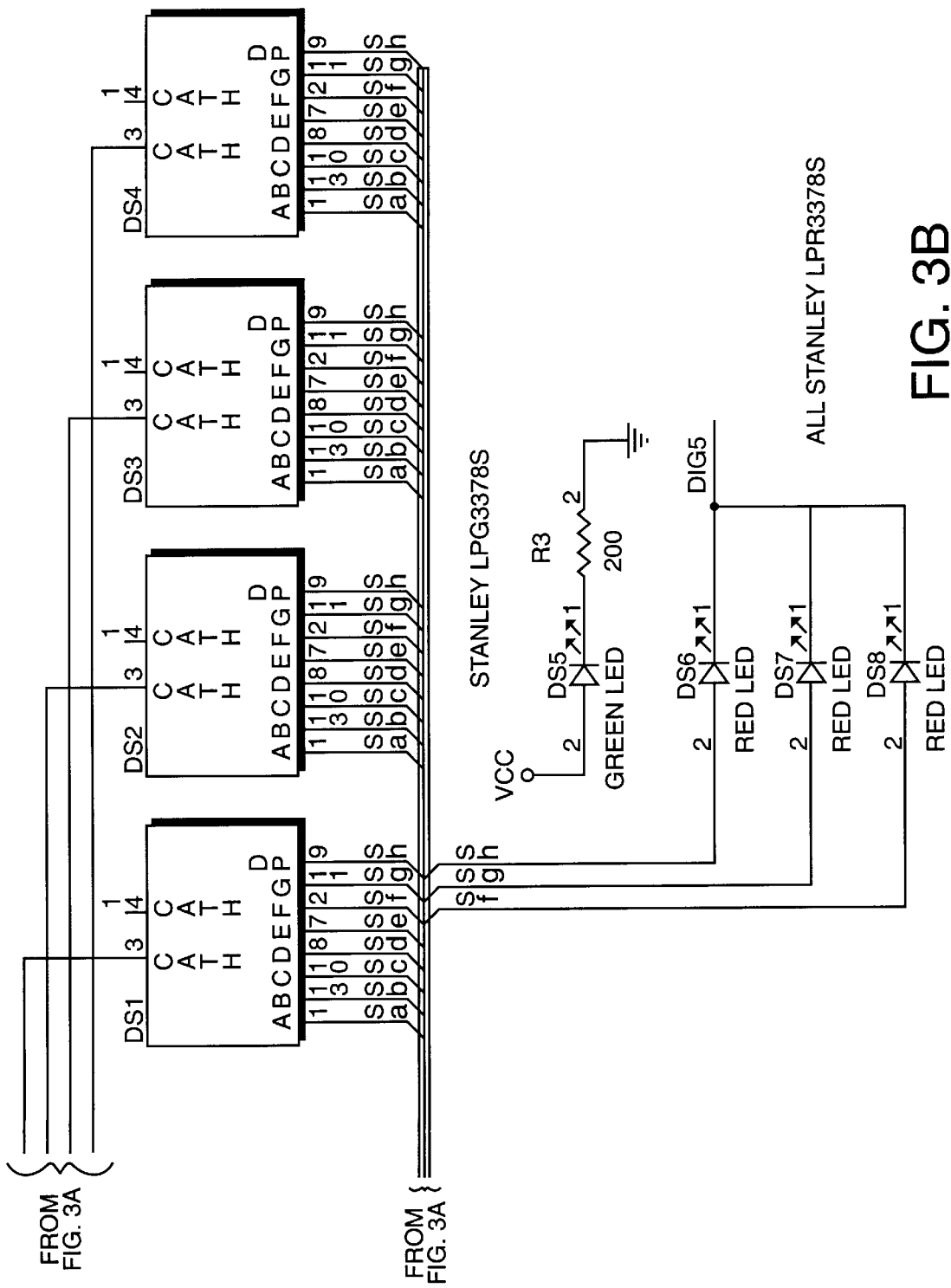
Figure 3C:
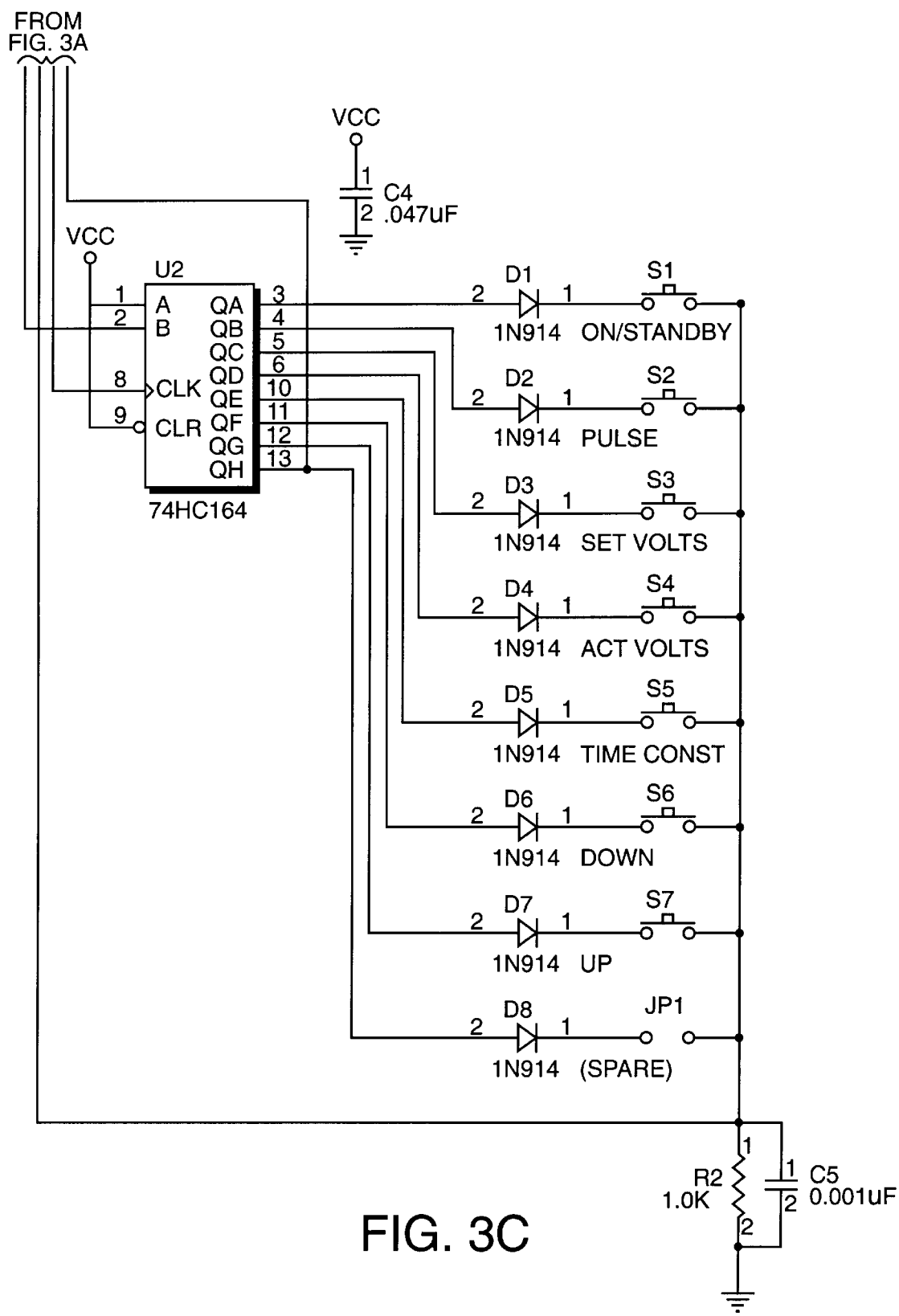
Figure 4A:
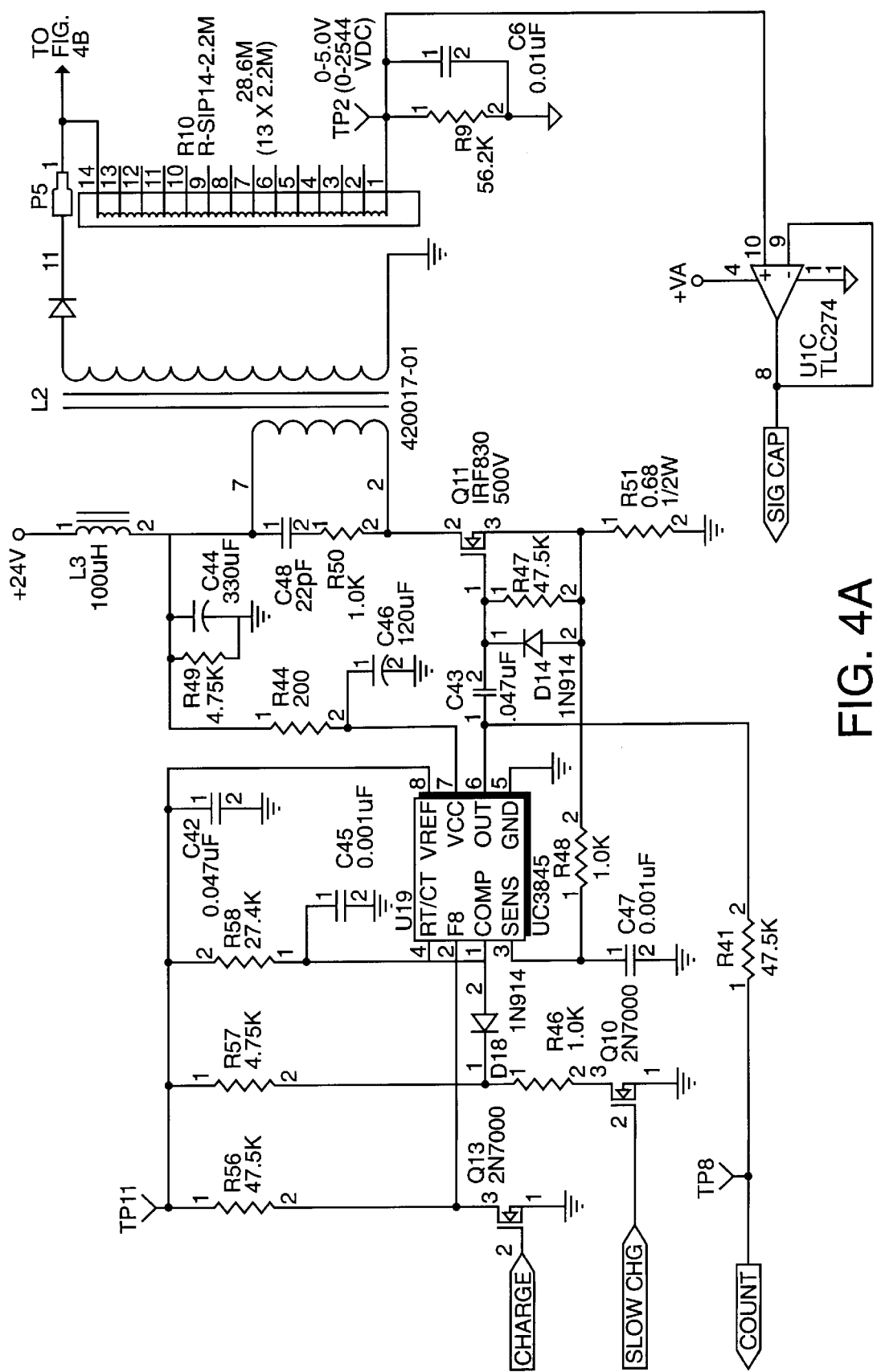
FIG. 4 illustrates a block diagram schematic of the high voltage section of the preferred embodiment of the present invention.
Figure 4B:
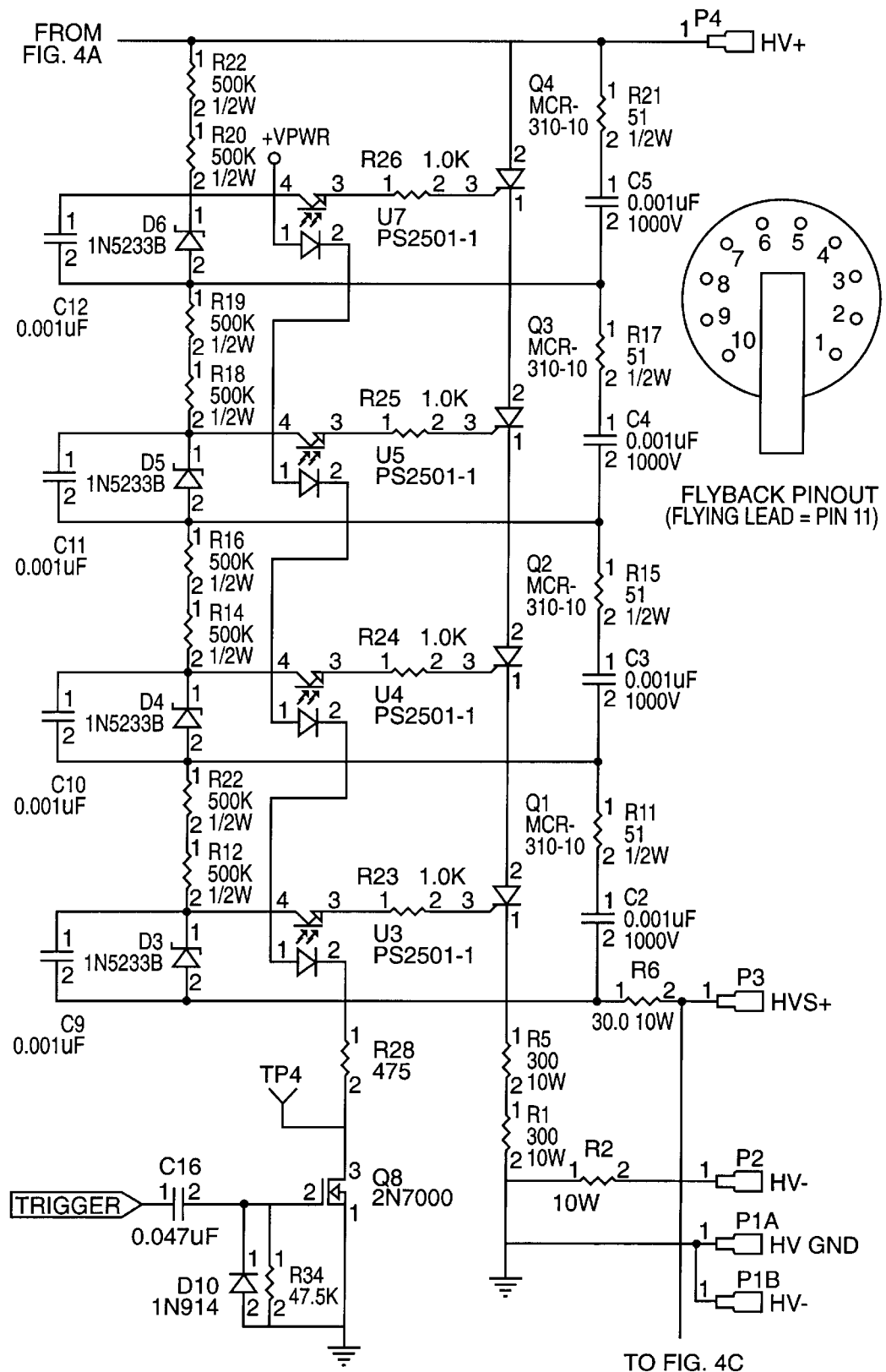
Figure 4C:
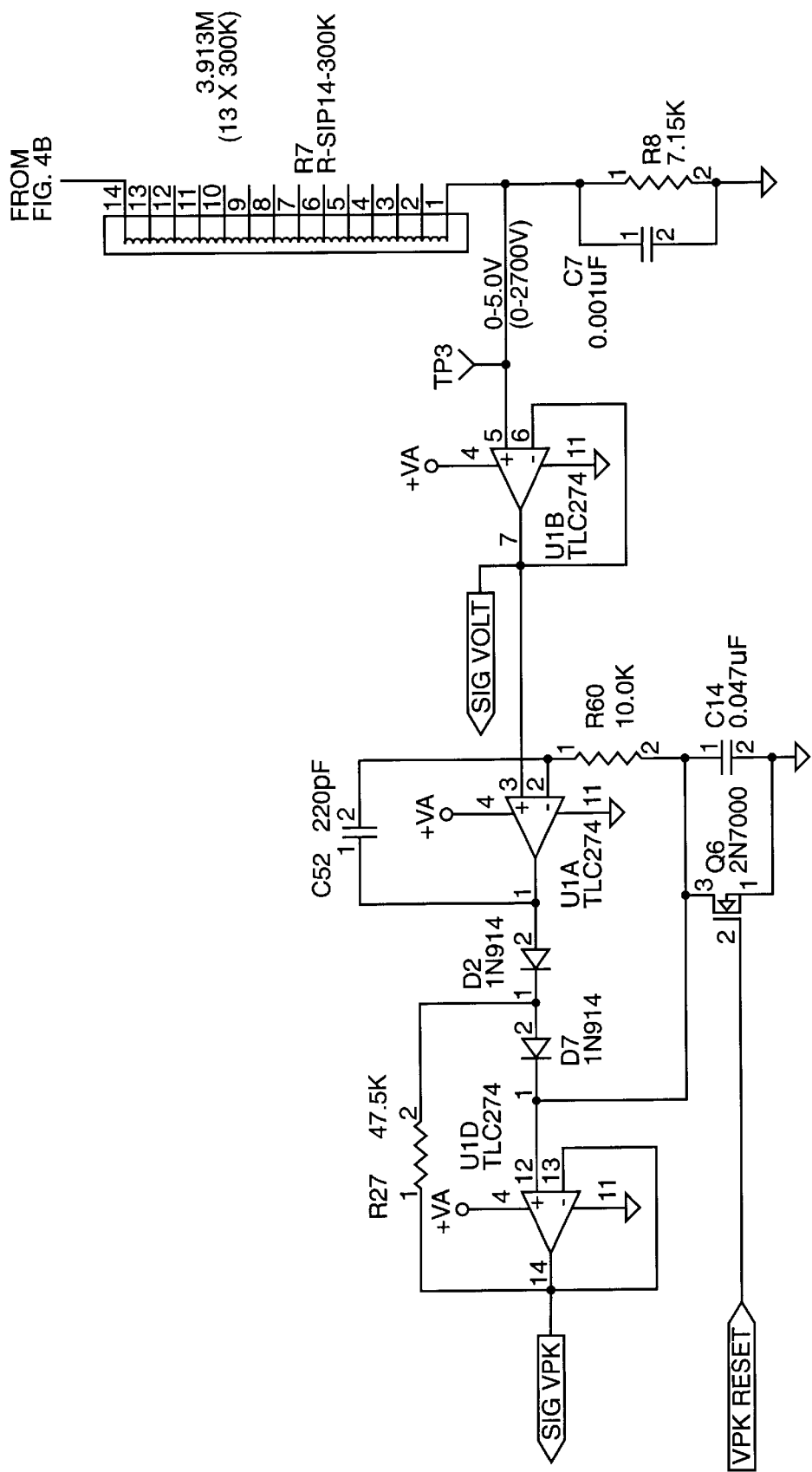
Figure 5A:
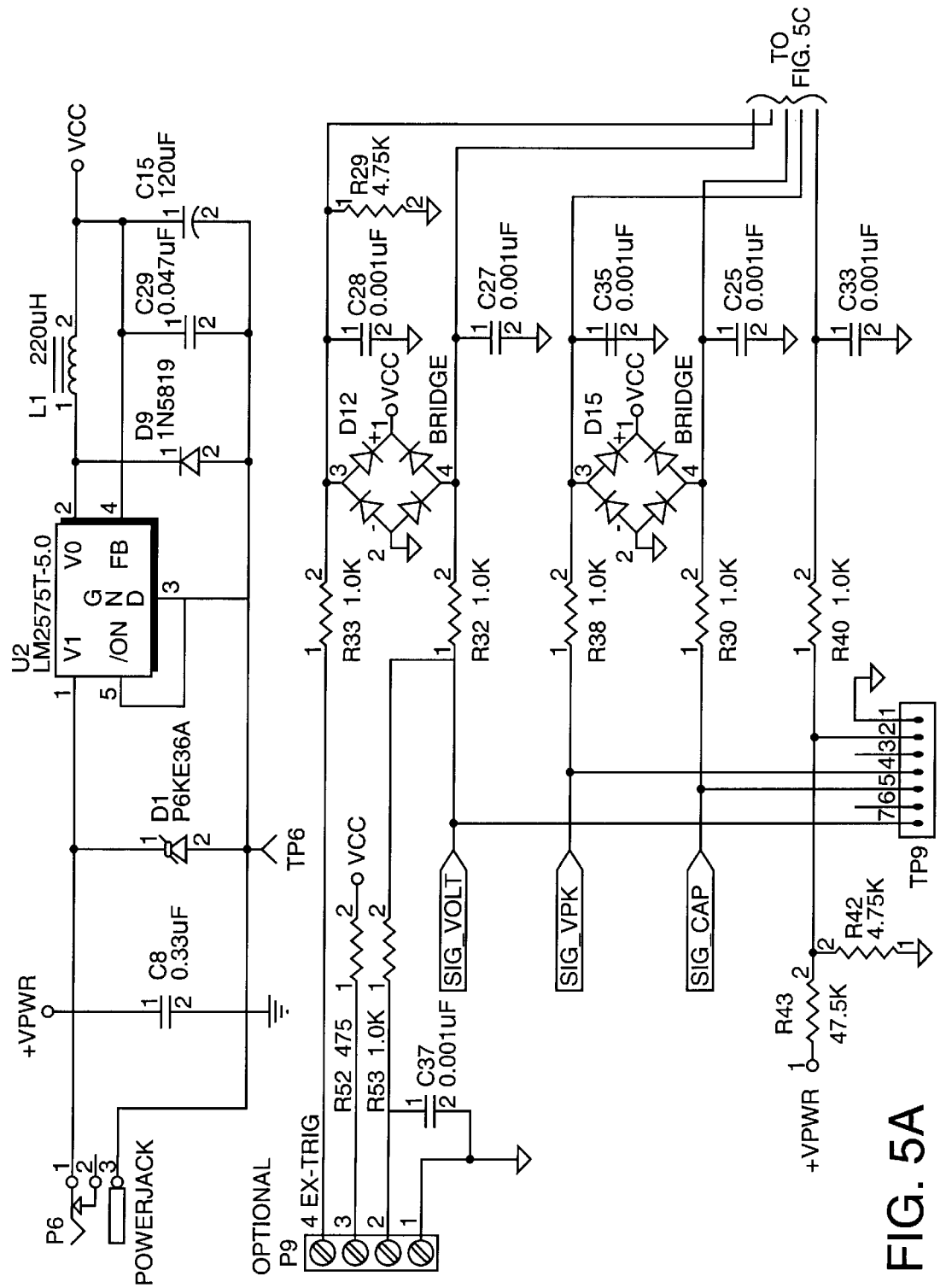
FIG. 5 illustrates a block diagram schematic of the digital control section of the preferred embodiment of the present invention.
Figure 5B:
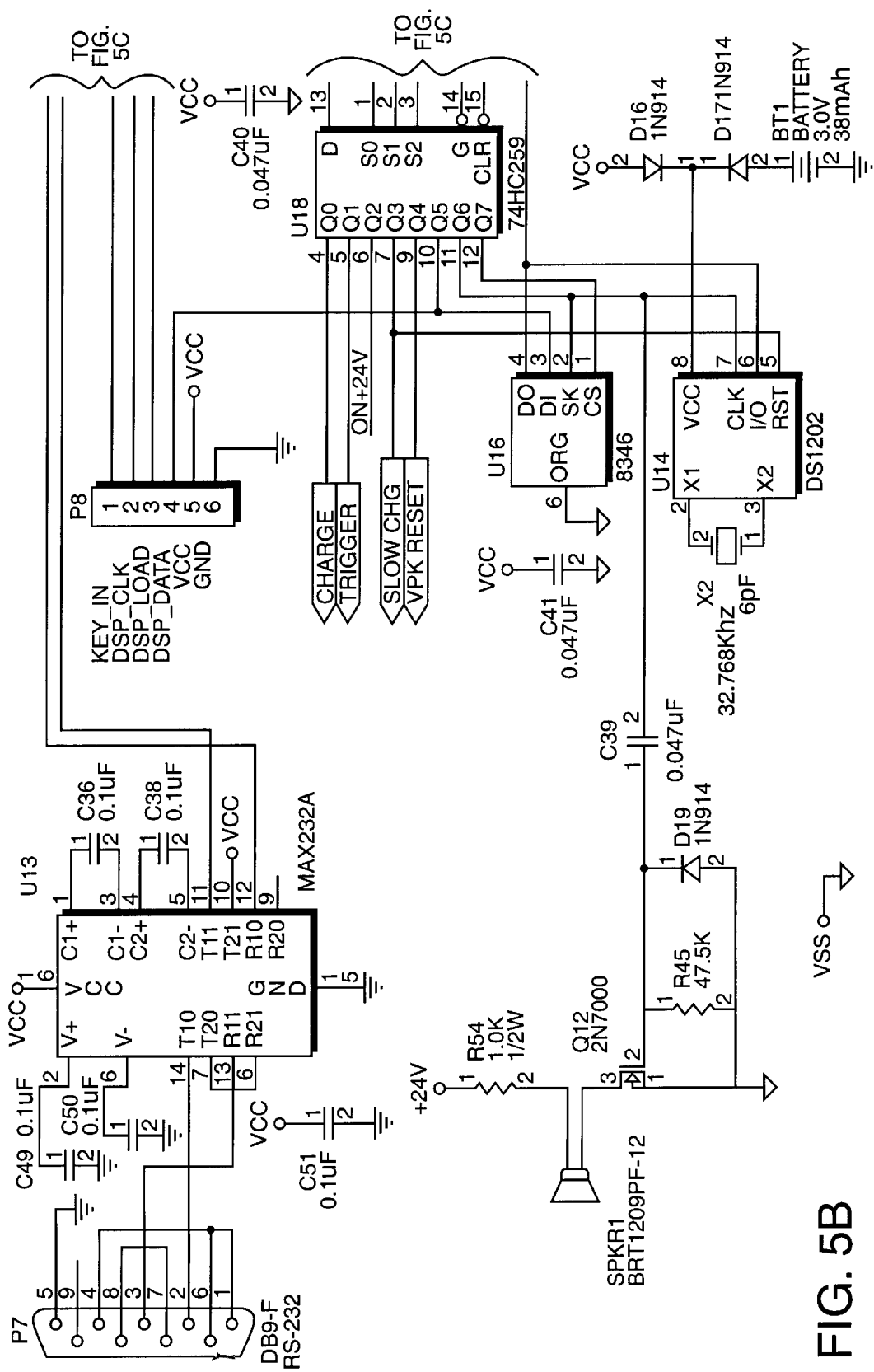
Figure 5C:
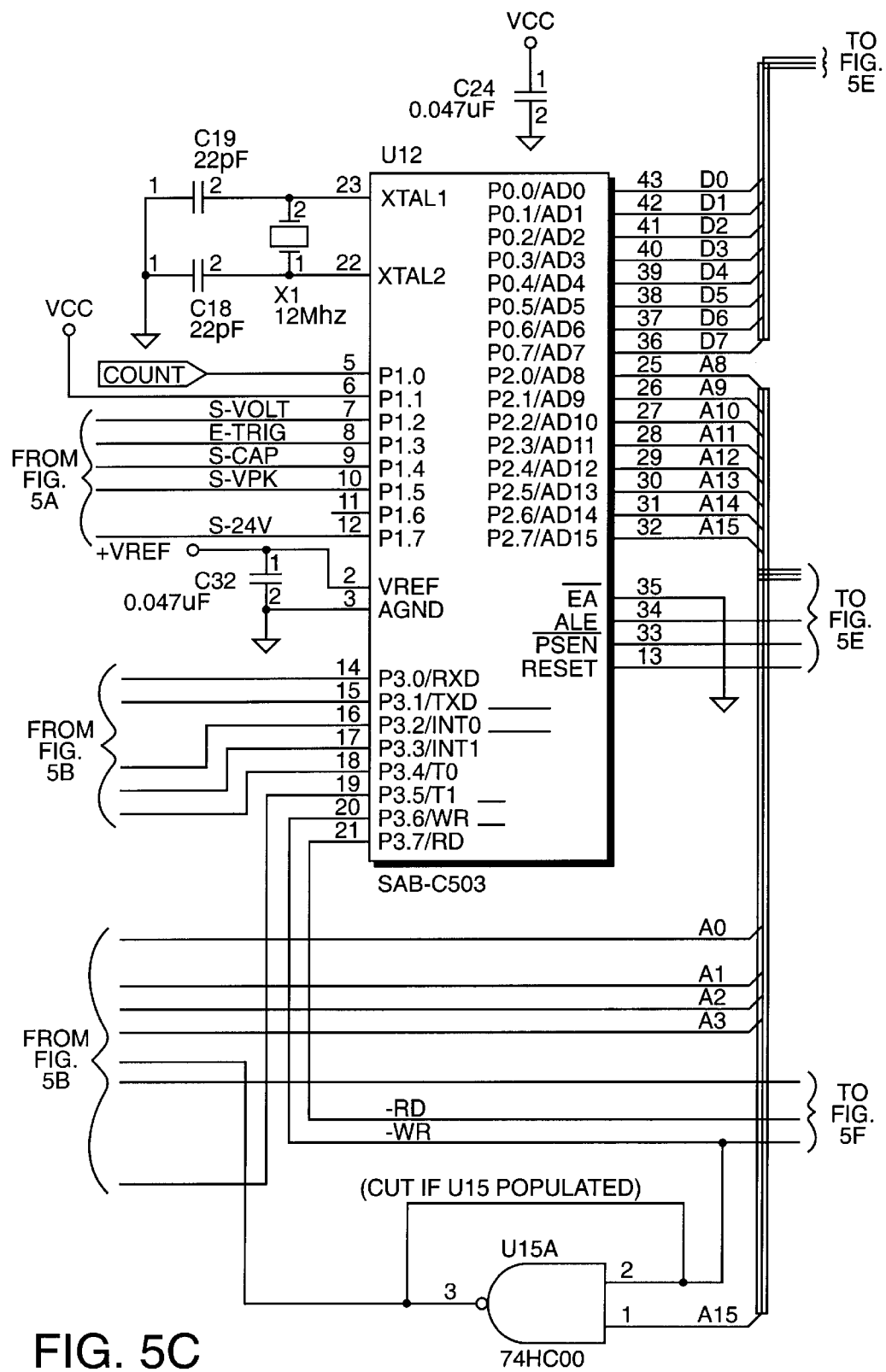
Figure 5D:
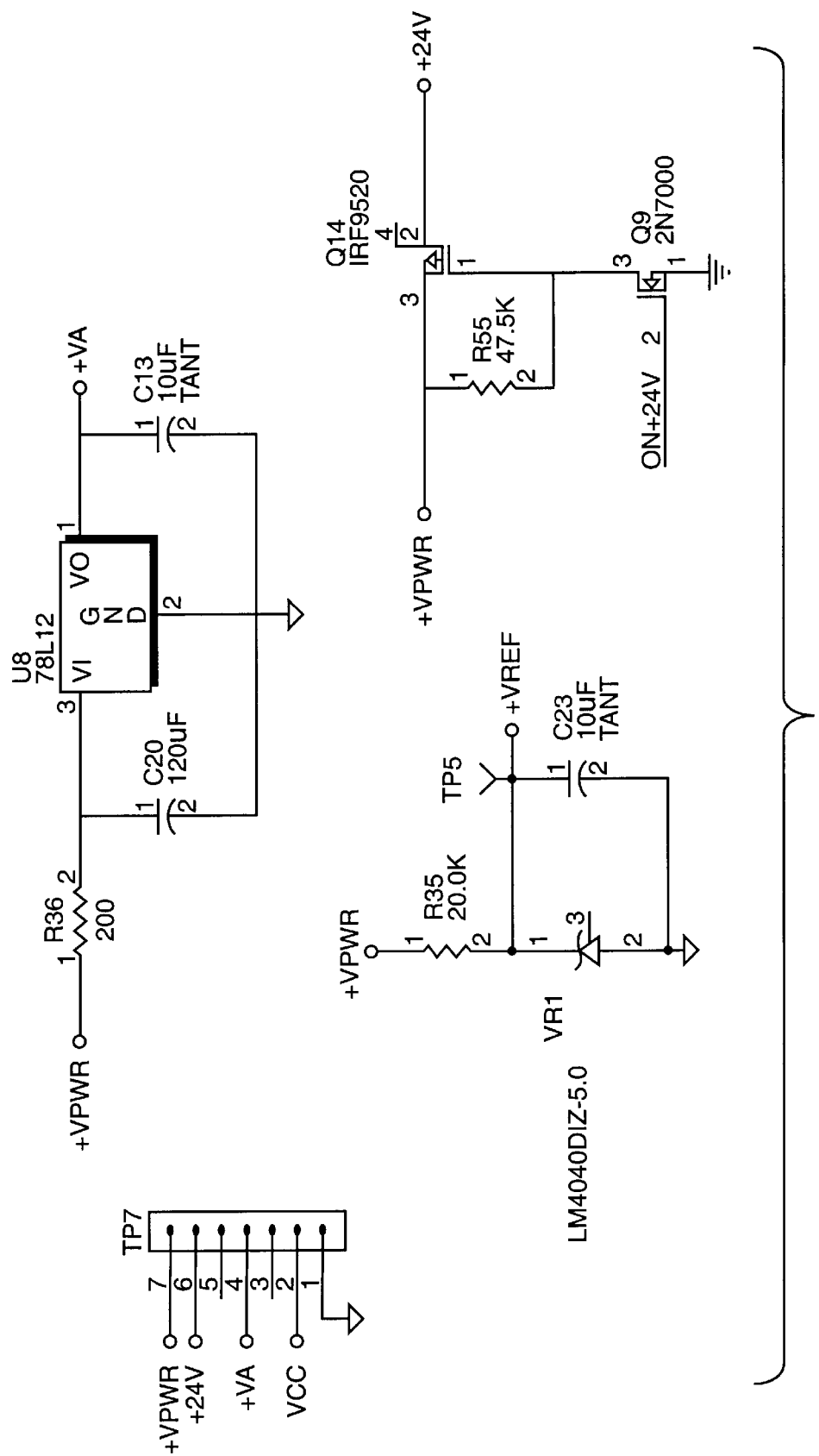
Figure 5E:
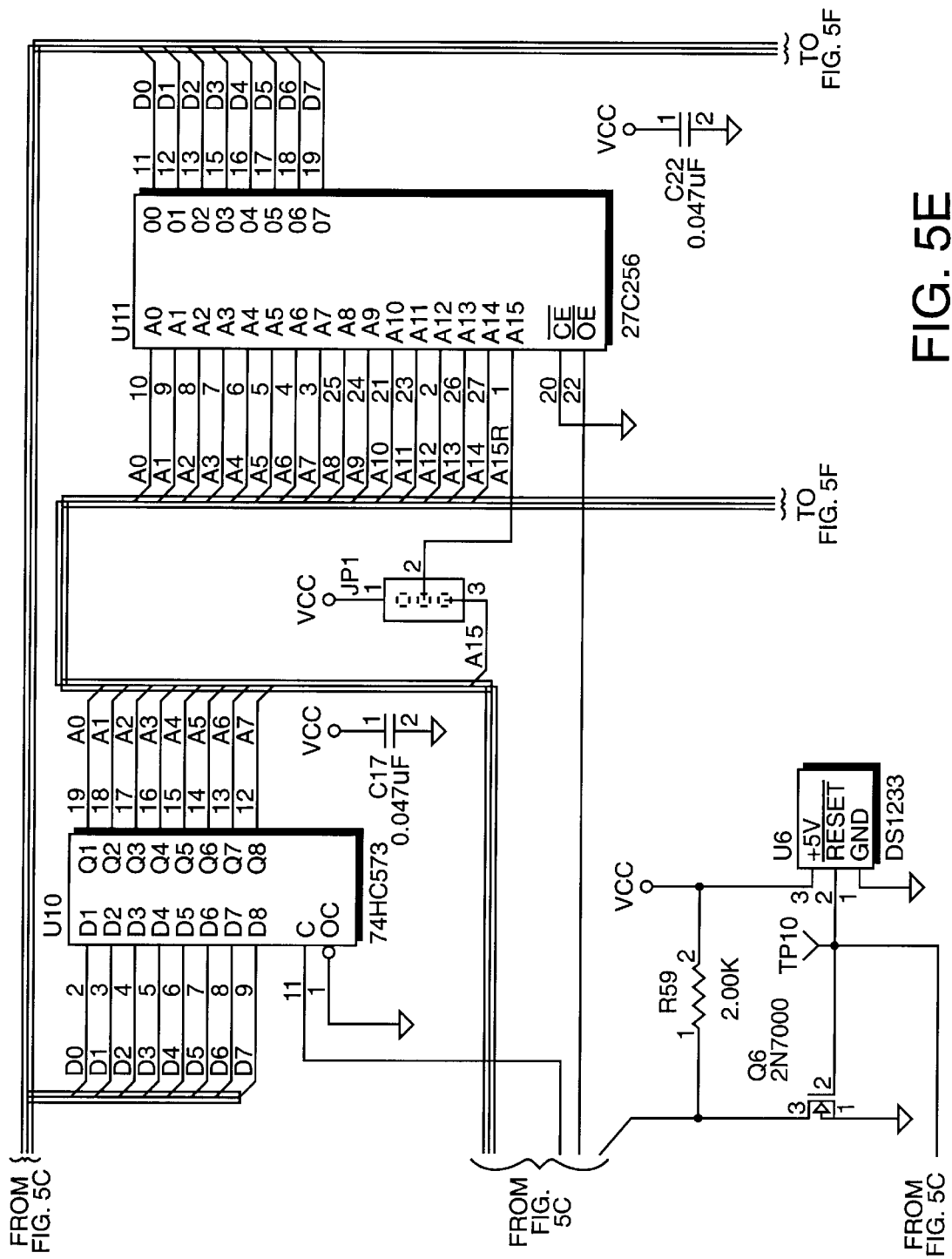
Figure 5F:
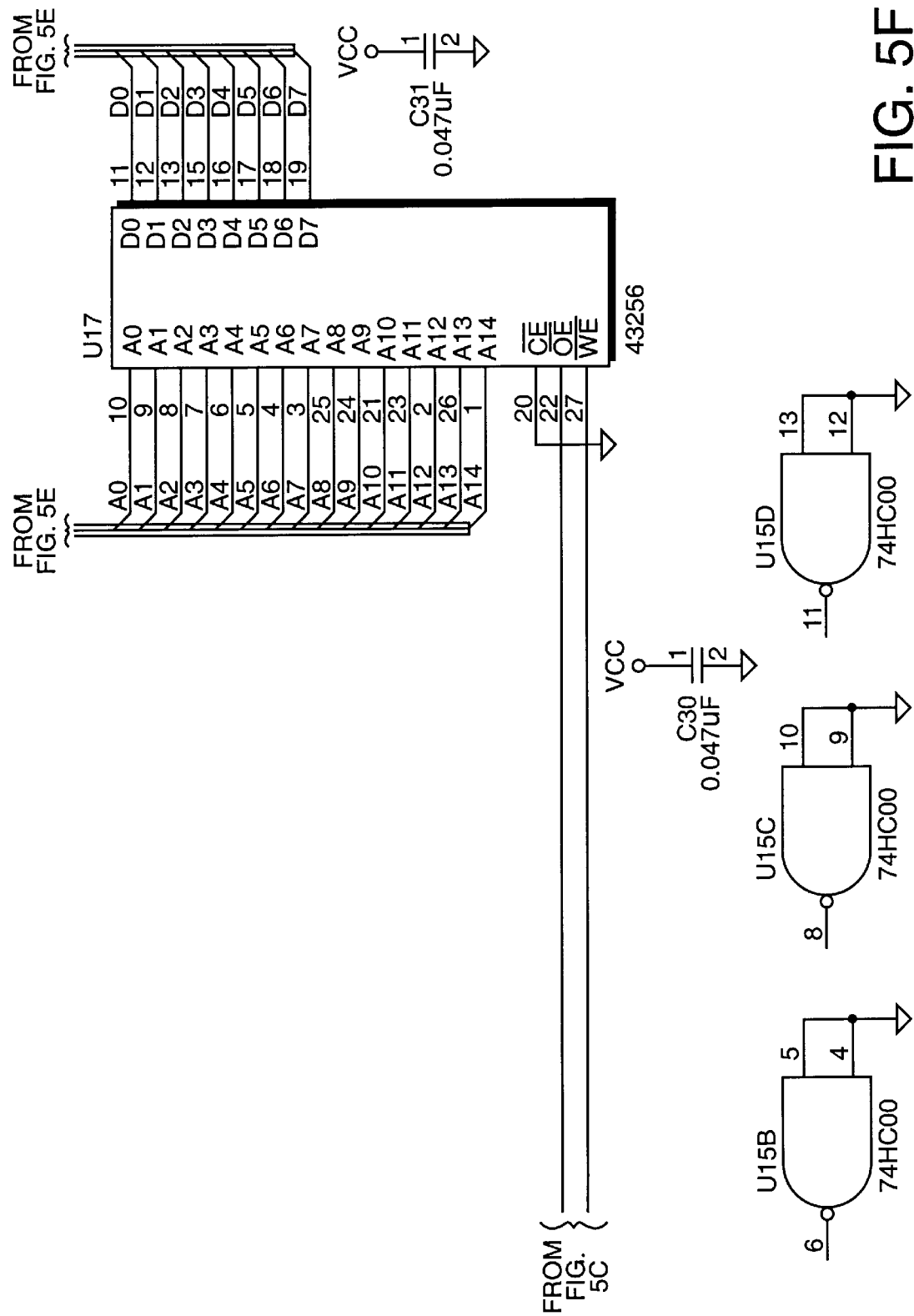
Figure 6:
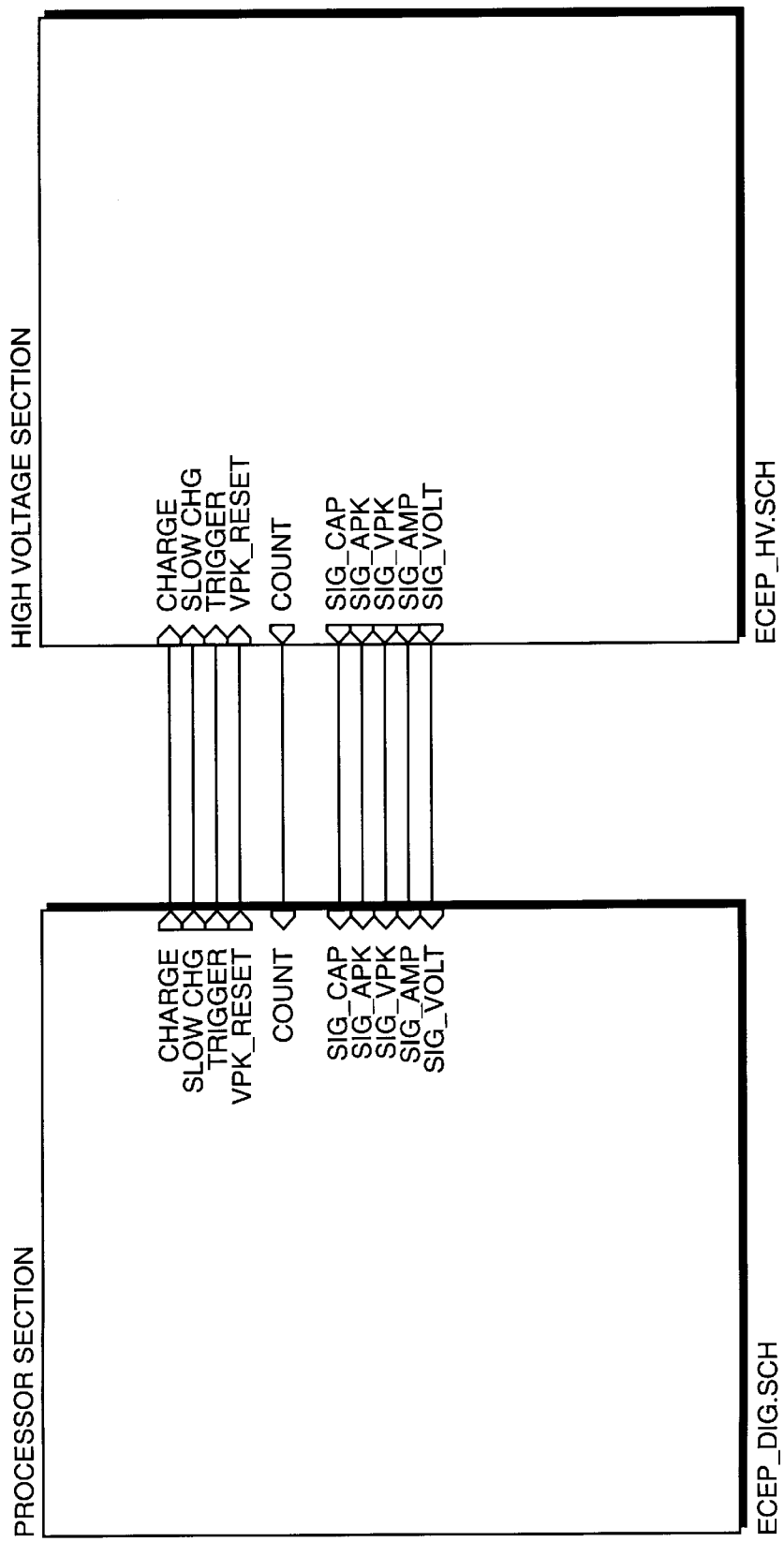
FIG. 6 illustrates a block diagram schematic of the main circuit board couplings of the preferred embodiment of the present invention.

FIGS. 3 through 6 illustrate detailed block diagram schematics of portions of the circuitry of the preferred embodiment of the present invention. FIG. 3 illustrates a block diagram schematic of the display board circuitry of the preferred embodiment of the present invention. FIG. 4 illustrates a block diagram schematic of the high voltage section of the preferred embodiment of the present invention. FIG. 5 illustrates a block diagram schematic of the digital control section of the preferred embodiment of the present invention. FIG. 6 illustrates a block diagram schematic of the main circuit board couplings of the preferred embodiment of the present invention.

EXAMPLE 1

The following tables, Table 1 and Table 2, are included to show the benefits of electroporation, using an electroporator according to the present invention, over classical chemical protocols. The difference in transformation efficiency for different strains of *E.coli* is illustrated in Table 1. As illustrated, in each case, the transformation efficiency is markedly improved for the electroporation method. The time required for each step is compared in Table 2. As illustrated, the time to complete a transformation by electroporation is much less than the time to complete a transformation using the chemical method.

Appendix 1 includes Version 1.0 of the User Manual for the Electroporator 2510. The Electroporator 2510 is the first commercial embodiment of an electroporator according to the teachings of the present invention. The Electroporator 2510 and the User Manual are both available from Eppendorf Scientific, Inc., University Research Park, 545 Science Drive, Madison, Wis., 53711.

The present invention has been described in terms of specific embodiments incorporating details to facilitate the understanding of the principles of construction and operation of the invention. Such reference herein to specific embodiments and details thereof is not intended to limit the scope of the claims appended hereto. It will be apparent to those skilled in the art that modifications may be made in the embodiment chosen for illustration without departing from the spirit and scope of the invention.

TABLE 1

Transformation Efficiencies For Electroporation And Chemical Methods

| E. coli Strain | Method | Field Strength (kV/cm) | Transformation Efficiency (Transformants/µg) |
|---|---|---|---|
| C600 | Electro | 19 | $2 \times 10^9$ |
|  | Chem | n/a | $2 \times 10^7$ |
| K12 | Electro | 17 | $3.5 \times 10^9$ |
|  | Chem | n/a | $6 \times 10^6$ |
| DH5α | Electro | 17 | $3 \times 10^9$ |
|  | Chem | n/a | $3 \times 10^7$ |
| DH10B | Electro | 16.6 | $4 \times 10^9$ |
|  | Chem | n/a | $9 \times 10^6$ |

TABLE 2

Time Comparison For Transformations

| Procedure | Electroporation | Chemical |
|---|---|---|
| Mix DNA And Bacteria | 30 sec. | 30 sec. |
| Incubate On Ice | n/a | 20–30 min. |
| Pulse | 10 sec. | n/a |
| Heat Shock | n/a | 2 min. |
| Add Medium | 30 sec. | 30 sec. |
| Total Time Required | 1 min., 10 sec. | 28 min. |

What is claimed is:

1. An apparatus for electroporation for delivering a predetermined charge to a suspension of cells comprising DNA and cloned DNA for combining the cloned DNA with the cells comprising DNA, the apparatus comprising:
   a. means for generating pulses of a controlled amount of energy;
   b. means for coupling the pulses to a capacitor, the means for coupling coupled to the means for generating and to the capacitor;
   c. means for counting the number of pulses necessary to store a predetermined charge on the capacitor, the means for counting coupled to the means for generating and to the means for coupling for counting the number of pulses coupled to the capacitor;
   d. means for measuring a charge stored on the capacitor when a threshold value is reached, the means for measuring coupled to the capacitor;
   e. means for calculating a charge per each of the pulses value and a remaining number of pulses required to completely store the predetermined charge on the capacitor, the means for calculating coupled to the means for counting and to the means for measuring;
   f. means for controlling coupled to the means for calculating, to the means for generating and to the means for coupling, for controlling the generation and coupling of the remaining number of pulses to the capacitor; and
   g. means for transferring energy stored on the capacitor to a cuvette after the remaining number of pulses have been coupled to the capacitor, wherein the means for transferring is coupled to the capacitor, to the load and to the means for controlling, and further wherein the means for controlling also controls the means for transferring.

2. The apparatus as claimed in claim 1 wherein said means for generating pulses is capable of transferring a constant amount of energy with each pulse.

3. The apparatus as claimed in claim 1 further comprising means for monitoring coupled to the means for controlling and to the cuvette for monitoring a voltage level and a current level at the cuvette.

4. The apparatus as claimed in claim 1 wherein the means for calculating further calculates an impedance value at the cuvette.

5. The apparatus as claimed in claim 4 further comprising means for determining coupled to the means for monitoring and to the means for controlling for determining if the impedance value is within an acceptable range.

6. The apparatus as claimed in claim 5 further comprising a display coupled to the means for controlling and to the means for determining for displaying the impedance value and an error message if the impedance value is not within the acceptable range.

7. The apparatus as claimed in claim 6 wherein the threshold value is a predetermined number of pulses.

8. The apparatus as claimed in claim 6 wherein the threshold value is a predetermined level of charge stored on the capacitor.

* * * * *